(12) United States Patent
Amorelli et al.

(10) Patent No.: US 9,758,467 B2
(45) Date of Patent: Sep. 12, 2017

(54) ORGANOLEPTIC COMPOUNDS

(71) Applicant: INTERNATIONAL FLAVORS & FRAGRANCES INC., New York, NY (US)

(72) Inventors: Benjamin Amorelli, Brielle, NJ (US); Edward Arruda, Easton, PA (US); Robert Belko, Monroe, NJ (US); Tingwei Cai, Holmdei, NJ (US); Adam Closson, Jersey City, NJ (US); Nicole Giffin, Hazlet, NJ (US); Gary Mertz, Robbinsville, NJ (US); Michael Monteleone, Hazlet, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 15/041,112

(22) Filed: Feb. 11, 2016

(65) Prior Publication Data
US 2016/0160153 A1    Jun. 9, 2016

Related U.S. Application Data

(62) Division of application No. 14/465,993, filed on Aug. 22, 2014, now Pat. No. 9,289,366.

(60) Provisional application No. 61/869,060, filed on Aug. 22, 2013.

(51) Int. Cl.
| | | |
|---|---|---|
| A61K 8/00 | (2006.01) |
| C07C 69/75 | (2006.01) |
| A61K 8/49 | (2006.01) |
| C11B 9/00 | (2006.01) |
| C11D 3/50 | (2006.01) |
| A61K 8/36 | (2006.01) |
| A61K 8/33 | (2006.01) |
| A61Q 5/02 | (2006.01) |
| A61Q 19/10 | (2006.01) |
| A61Q 11/00 | (2006.01) |
| C07D 307/87 | (2006.01) |
| C07C 47/21 | (2006.01) |
| C07D 307/83 | (2006.01) |
| C07C 69/96 | (2006.01) |
| C07C 43/162 | (2006.01) |
| C07C 69/60 | (2006.01) |
| C07C 49/385 | (2006.01) |
| C07C 49/587 | (2006.01) |
| A61Q 13/00 | (2006.01) |
| C11D 3/20 | (2006.01) |
| A61K 8/37 | (2006.01) |
| A61Q 5/00 | (2006.01) |
| A61Q 15/00 | (2006.01) |
| A61Q 19/00 | (2006.01) |

(52) U.S. Cl.
CPC ............ *C07C 69/75* (2013.01); *A61K 8/33* (2013.01); *A61K 8/36* (2013.01); *A61K 8/37* (2013.01); *A61K 8/498* (2013.01); *A61Q 5/00* (2013.01); *A61Q 5/02* (2013.01); *A61Q 11/00* (2013.01); *A61Q 13/00* (2013.01); *A61Q 15/00* (2013.01); *A61Q 19/00* (2013.01); *A61Q 19/10* (2013.01); *C07C 43/162* (2013.01); *C07C 47/21* (2013.01); *C07C 49/385* (2013.01); *C07C 49/587* (2013.01); *C07C 69/60* (2013.01); *C07C 69/96* (2013.01); *C07D 307/83* (2013.01); *C07D 307/87* (2013.01); *C11B 9/0015* (2013.01); *C11B 9/0019* (2013.01); *C11B 9/0034* (2013.01); *C11B 9/0038* (2013.01); *C11B 9/0076* (2013.01); *C11D 3/2072* (2013.01); *C11D 3/50* (2013.01); *C07C 2101/08* (2013.01); *C07C 2101/14* (2013.01); *C07C 2101/16* (2013.01); *C07C 2101/18* (2013.01); *C07C 2102/42* (2013.01)

(58) Field of Classification Search
CPC .................................. A61K 8/33; C07C 47/21
See application file for complete search history.

(56) References Cited

PUBLICATIONS

S. Bonazzi et al., Journal of the American Chemical Society, 2010, vol. 132, issue 4, pp. 1432-1442 (abstract).*
M. Lorenz et al., Organic Letters, 2008, vol. 10, issue 19, pp. 4371-4374 (abstract).*
S. Bonazzi et al., Angewandte Chemie, International Edition, 2007, vol. 46, issue 45, pp. 8707-8710 (abstract).*
R. K. Boeckman et al., Journal of the American Chemical Society, 2006, vol. 128, issue 34, pp. 11032-11033 (abstract).*

\* cited by examiner

*Primary Examiner* — John Hardee
(74) *Attorney, Agent, or Firm* — Martin Zhang; XuFan Tseng; Elizabeth M. Stover

(57) ABSTRACT

The present invention relates to novel compounds and their use as fragrance materials.

17 Claims, No Drawings

ORGANOLEPTIC COMPOUNDS

STATUS OF RELATED APPLICATIONS

This application is a divisional of U.S. Ser. No. 14/465,993, filed Aug. 22, 2014, now U.S. Pat. No. 9,289,366, which is a continuation of U.S. provisional application 61/869,060 filed Aug. 22, 2013, the contents hereby incorporated by references as if set forth in their entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, an embodiment of the present invention relates to novel isobenzofuran compounds represented by Formula I, 1,1-diethyl-4,6-dimethyl-1,3,3a,4(or 6),7,7a-hexahydro-isobenzofuran, including Formula Ia and Ib and Formula II, 1,1-diethyl-5,7-dimethyl-1,3,3a,4,5(or 7),7a-hexahydro-isobenzofuran, including Formula IIa and IIb, which exhibit unexpected woody and spicy notes with leather-like quality, and a method of improving, enhancing or modifying a fragrance formulation through the addition of an olfactory acceptable amount of these isobenzofurans.

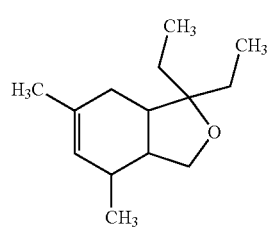

Formula Ia

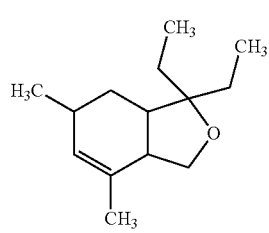

Formula Ib

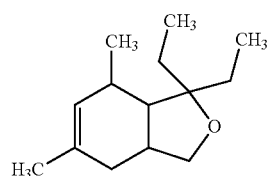

Formula IIa

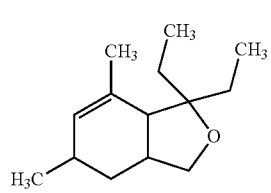

Formula IIb

Another embodiment of the present invention relates to the advantageous fragrance use of a mixture of Formula III, cyclopentadecanone, and Formula IV, cyclopentadec-3-enone, which exhibits strong and creamy musk, musk ketone, caring and woody notes with an interesting floralcy character. Their structures are set forth below:

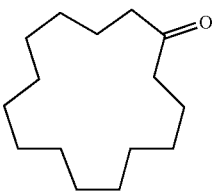

Formula III

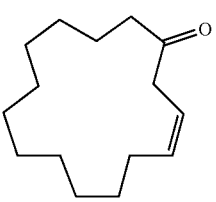

Formula IV

Another embodiment of the present invention relates to novel aldehydes represented by Formula V, 5-methyl-hept-5-enal, and Formula VI, 2,4-dimethyl-hex-4-enal, which exhibit unexpected strong and complex fragrance effect of a melon-like ozonic note with a green aspect that provides a natural melon feel and a vegetable character, and a method of improving, enhancing or modifying a fragrance formulation through the addition of an olfactory acceptable amount of theses aldehydes.

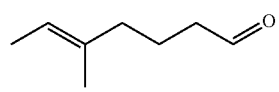

Formula V

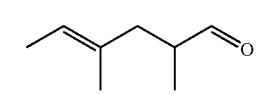

Formula VI

Another embodiment of the present invention relates to a novel aldehyde 2,4,8-trimethyl-deca-4,9-dienal represented by Formula VII, which exhibits unexpected powerful aldehydic green, floral and muguet notes with high impact and very toppy characters, and a method of improving, enhancing or modifying a fragrance formulation through the addition of an olfactory acceptable amount of this aldehyde.

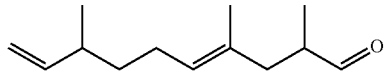

Formula VII

Another embodiment of the present invention relates to novel benzofuranones represented by Formula VIII, 5-ethyl-3-methylhexahydro-1-benzofuran-2(3H)-one, and Formula IX, 6-ethyl-3-methylhexahydro-1-benzofuran-2(3H)-one, which exhibit unexpected creamy, coconut-like and pleasant notes supported by an overall woodiness and a slightly animalic character, reminiscent of heliotropin and coumarin, and a method of improving, enhancing or modifying a fragrance formulation through the addition of an olfactory acceptable amount of theses benzofuranones.

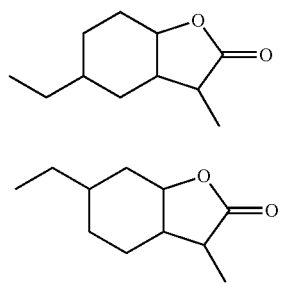

Formula VIII

Formula IX

Another embodiment of the present invention relates to a novel compound methyl-2-(propan-2-yl)cyclohexyl carbonate represented by Formula X, which exhibits unexpected apple and berry notes with a soft fruity character further supported by a herbaceous, spicy, fresh and woody quality, and a method of improving, enhancing or modifying a fragrance formulation through the addition of an olfactory acceptable amount of this compound.

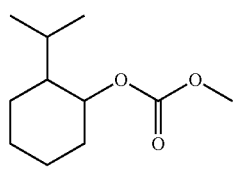

Formula X

Another embodiment of the present invention relates to a novel compound 2-[3-methoxy-2-propen-1-yl]-6,6-dimethyl-bicyclo[3.1.1]hept-2-ene represented by Formula XI, which exhibits unexpected white floral and muguet characters topped by fresh, green and melon-like notes further supported by creamy and herbaceous quality, and a method of improving, enhancing or modifying a fragrance formulation through the addition of an olfactory acceptable amount of this compound.

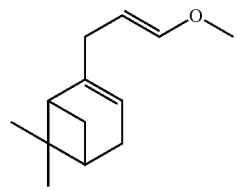

Formula XI

Another embodiment of the present invention relates to a novel compound but-2-enoic acid 1-cyclopentyl-ethyl ester represented by Formula XII, which exhibits unexpected fruity, green and fresh accord with wine-like woody, spicy and sweet notes, very toppy and multifaceted, and a method of improving, enhancing or modifying a fragrance formulation through the addition of an olfactory acceptable amount of this ethyl ester.

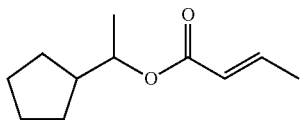

Formula XII

Another embodiment of the present invention relates to novel compounds represented by Formula XIII, 1,2,4-trimethyl-cyclohex-3-enecarboxylic acid ethyl ester, and Formula XIV, 1,3,5-trimethyl-cyclohex-3-enecarboxylic acid ethyl ester, which exhibit unexpected complex fragrance effect of fruity, cassis (black currant)-like, added freshness of citrus (grape fruit), slightly earthy and herbaceous with an olibanum aspect, and a method of improving, enhancing or modifying a fragrance formulation through the addition of these ethyl esters.

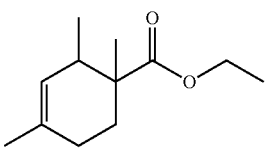

Formula XIII

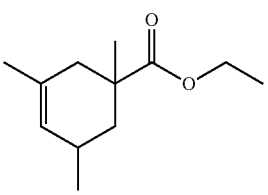

Formula XIV

Another embodiment of the present invention relates to a novel compound 13-methyl-3a,4,5,6,7,8,9,10,11,13a-decahydro-1H,3H-2-oxa-cyclopentacyclododecene represented by Formula XV, which exhibits an interesting combination of fruity, woody, musky, clean, green, fresh, sweet and animalic notes, very desirable, caring, sensual, very powdery and soft with a unique tobacco-like quality. Its ambery and musky notes provide additional body, and a method of improving, enhancing or modifying a fragrance formulation through the addition of an olfactory acceptable amount of this compound.

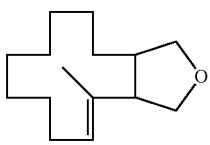

Formula XV

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation of the compounds of the present invention is detailed in the Examples. Materials were purchased from Aldrich Chemical Company unless noted otherwise.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, psi is understood to be pound-force per square inch, and mmHg be millimeters (mm) of mercury (Hg). IFF as used in the examples is understood to mean International Flavors & Fragrances Inc., New York, N.Y., USA.

Example I

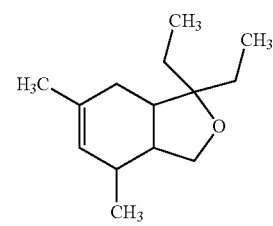

Formula Ia

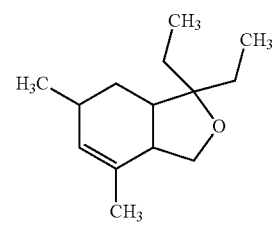

Formula Ib

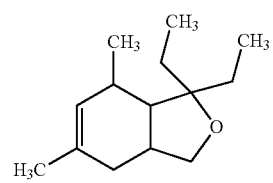

Formula IIa

-continued

Formula IIb

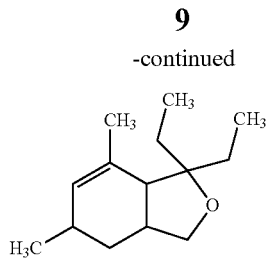

Preparation of 1,1-Diethyl-4,6-dimethyl-1,3,3a,4,7,7a-hexahydro-isobenzofuran (Formula Ia), 1,1-Diethyl-4,6-dimethyl-1,3,3a,6,7,7a-hexahydro-isobenzofuran (Formula Ib), 1,1-Diethyl-5,7-dimethyl-1,3,3a,4,7,7a-hexahydro-isobenzofuran (Formula IIa) and 1,1-Diethyl-5,7-dimethyl-1,3,3a,4,5,7a-hexahydro-isobenzofuran (Formula IIb)

A mixture of Formula I 1,1-diethyl-4,6-dimethyl-1,3,3a,4(or 6),7,7a-hexahydro-isobenzofuran including Formula Ia and Ib and Formula II 1,1-diethyl-5,7-dimethyl-1,3,3a,4,5(or 7),7a-hexahydro-isobenzofuran including Formula IIa and IIb was prepared as described in EXAMPLE V of U.S. application Ser. No. 13/888,713 filed May 7, 2013. Formula I and Formula II had a weight ratio of about 80:20.

The mixture obtained in the above preparation possessed the NMR spectral characteristics of: $^1$H NMR (500 MHz, CDCl$_3$): 5.11-5.89 ppm (m, 1H), 2.89-4.06 ppm (m, 2H), 2.50 & 2.59 ppm (2s, 1H), 1.80-2.41 ppm (m, 2H), 1.62-1.79 ppm (m, 5H), 1.19-1.62 ppm (m, 4H), 0.82-1.17 ppm (m, 9H).

The mixture of Formula I and II was described as having woody and spicy notes with leather-like quality.

Example II

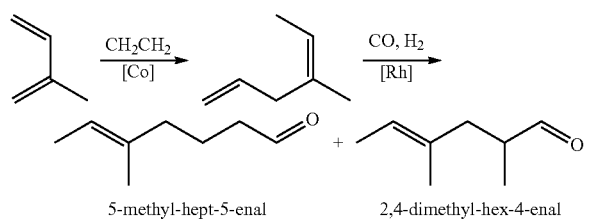

5-methyl-hept-5-enal     2,4-dimethyl-hex-4-enal

Preparation of 5-Methyl-hept-5-enal (Formula V) and 2,4-Dimethyl-hex-4-enal (Formula VI)

Isoprene reacted with ethylene gas in the presence of an appropriate cobalt catalyst to yield 4-methyl-hexa-1,4-diene, which was then subjected to hydroformylation reaction to afford the mixture of 5-methyl-hept-5-enal and 2,4-dimethyl-hex-4-enal.

Formula V obtained in the above preparation possessed the NMR spectral characteristics of: $^1$H NMR (400 MHz, CDCl$_3$): 9.77 (t, J=1.8 Hz, 1H), 5.18-5.32 (m, 1H), 2.41 (td, J=7.3, 1.8 Hz, 2H), 2.08 (t, J=7.6 Hz, 2H), 1.53-1.78 (m, 8H)

Formula VI obtained in the above preparation possessed the NMR spectral characteristics of: $^1$H NMR (400 MHz, CDCl$_3$): 9.66 (d, J=1.9 Hz, 1H), 5.03-5.13 (m, 1H), 1.53-2.56 (m, 9H), 1.06 (d, J=6.9 Hz, 3H)

The mixture of Formula V and VI was described as having a melon-like ozonic note with a green aspect.

Example III

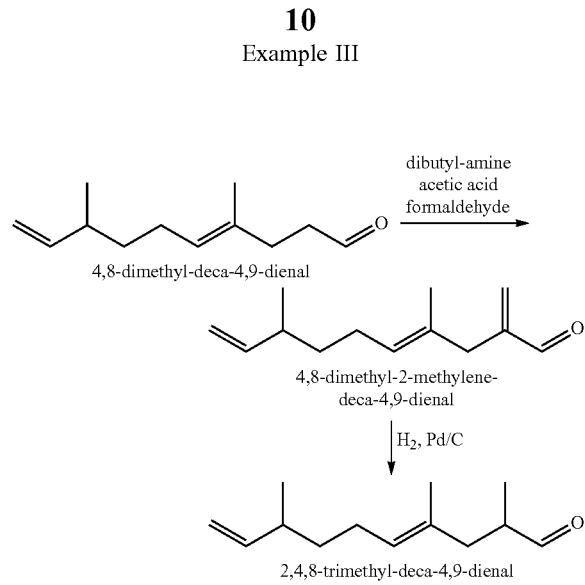

4,8-dimethyl-deca-4,9-dienal 4,8-dimethyl-2-methylene-deca-4,9-dienal 2,4,8-trimethyl-deca-4,9-dienal Preparation of 2,4,8-Trimethyl-deca-4,9-dienal (Formula VII)

4,8-Dimethyl-deca-4,9-dienal (commercially available at IFF) was used as the starting material to provide 4,8-dimethyl-2-methylene-deca-4,9-dienal, which was then hydrogenated to afford 2,4,8-trimethyl-deca-4,9-dienal.

$^1$H NMR (400 MHz, CDCl$_3$): 9.62 (d, J=2.0 Hz, 1H), 5.68 (ddd, J=17.4, 10.1, 7.7 Hz, 1H), 5.11-5.23 (m, 1H), 4.89-4.98 (m, 2H), 2.34-2.55 (m, 2H), 2.05-2.17 (m, 1H), 1.92-2.05 (m, 3H), 1.59 (s, 3H), 1.20-1.43 (m, 2H), 1.03 (d, J=6.8 Hz, 3H), 0.99 (d, J=6.8 Hz, 3H)

Formula VII was described as having green, floral and muguet notes.

Example IV

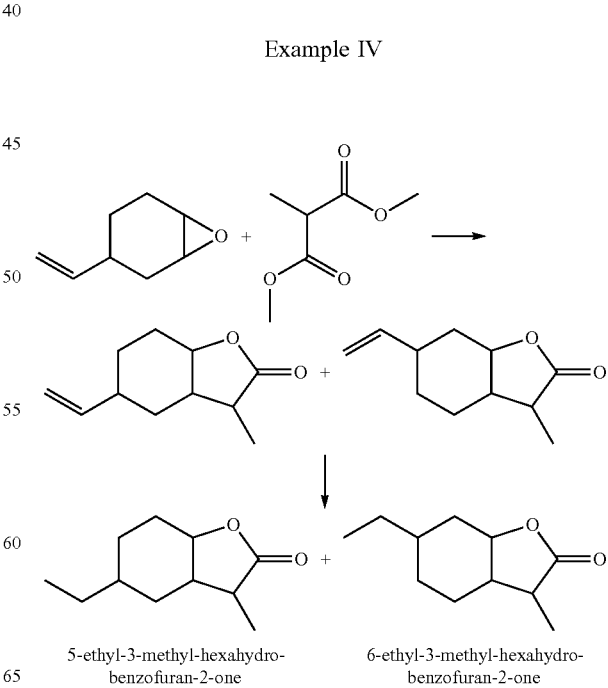

5-ethyl-3-methyl-hexahydro-benzofuran-2-one     6-ethyl-3-methyl-hexahydro-benzofuran-2-one Preparation of 5-Ethyl-3-methylhexahydro-1-benzofuran-2(3H)-one (Formula VIII) and 6-Ethyl-3-methylhexahydro-1-benzofuran-2(3H)-one (Formula IX)

4-Vinylcyclohexene oxide reacted with dimethyl methyl malonate in the presence of a base to afford the unsaturated lactone in the above, which was then subjected to hydrogenation to afford the isomeric mixture of 5-ethyl-3-methyl-hexahydro-1-benzofuran-2(3H)-one and 6-ethyl-3-methyl-hexahydro-1-benzofuran-2(3H)-one.

The mixture obtained in the above preparation possessed the NMR spectral characteristics of: $^1$H NMR (500 MHz, CDCl$_3$): 3.68-4.06 (m, 1H), 2.14-2.32 (m, 2H), 1.24-2.07 (m, 9H), 1.14-1.27 (m, 3H), 0.89-0.97 (m, 3H)

The mixture of Formula VIII and Formula IX was described as having creamy and coconut-like notes with woody and slightly animalic characters.

Example V

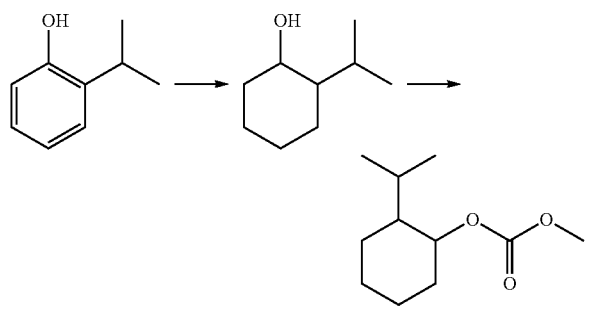

Preparation of Methyl-2-(propan-2-yl)cyclohexyl carbonate (Formula X)

2-Isopropyl phenol was hydrogenated to obtain 2-isopropyl cyclohexanol, which then reacted with an excess amount of dimethylcarbonate in the presence of catalyst sodium methoxide to afford methyl-2-(propan-2-yl)cyclohexyl carbonate.

$^1$H NMR (500 MHz, CDCl$_3$): 4.47-4.55 (m, 1H), 3.77 (s, 3H), 2.02-2.11 (m, 1H), 1.95 (m, 1H), 1.64-1.80 (m, 2H), 0.99-1.53 (m, 6H), 0.80-0.94 (m, 6H)

Formula X was described as having fruity, herbaceous, spicy, fresh and woody notes.

Example VI

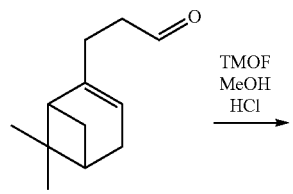

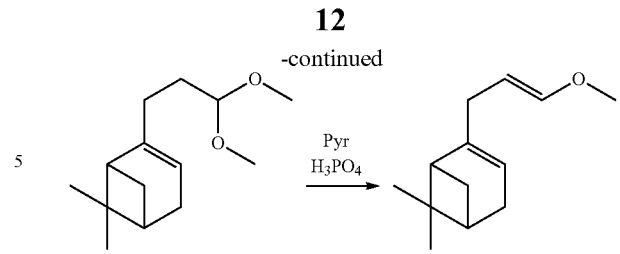

Preparation of 2-(3-Methoxy-2-propen-1-yl)-6,6-dimethyl-bicyclo[3.1.1]hept-2-ene (Formula XI)

Pinoacetaldehyde (commercially available at IFF) reacted with trimethylorthoformate (TMOF), methanol (MeOH) and hydrochloric acid (HCl) to obtain 2-(3,3-dimethoxypropyl)-6,6-dimethyl-bicyclo[3.1.1]hept-2-ene, which then, in the presence of pyridine (Pyr.) and phosphoric acid (H$_3$PO$_4$), to provide 2-(3-methoxy-2-propen-1-yl)-6,6-dimethyl-bicyclo[3.1.1]hept-2-ene.

$^1$H NMR (400 MHz, CDCl$_3$): 5.92 (dt, J=6.2, 1.6 Hz, 1H), 5.18-5.23 (m, 1H), 4.31 (td, J=7.3, 6.2 Hz, 1H), 3.58 (s, 3H), 2.69-2.76 (m, 2H), 1.97-2.39 (m, 4H), 1.26 (s, 3H), 1.12-1.17 (m, 1H), 0.82 (s, 3H)

Formula XI was described as having floral, muguet, fresh, green and melon-like notes with creamy and herbaceous quality.

Example VII

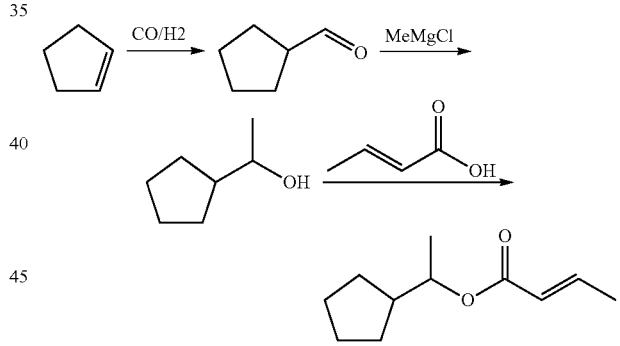

Preparation of But-2-enoic acid 1-cyclopentyl-ethyl ester (Formula XII)

Cyclopentene reacted with carbon monoxide (CO) and hydrogen (H$_2$) in the presence of a Wilkinson's catalyst to provide cyclopentanecarboxaldehyde, which then reacted with methylmagnesium chloride (MeMgCl) to provide 1-cyclopentylethanol, which further reacted with crotonic acid in the presence of p-toluenesulfonic acid (pTSA) to afford product but-2-enoic acid 1-cyclopentyl-ethyl ester.

$^1$H NMR (500 MHz, CDCl$_3$): 6.89-6.99 (m, 1H), 5.83 (dq, J=15.6, 1.6 Hz, 1H), 4.79-4.88 (m, 1H), 1.92-2.09 (m, 1H), 1.87 (dd, J=6.9, 1.5 Hz, 3H), 1.67-1.76 (m, 2H), 1.49-1.65 (m, 4H), 1.18-1.33 (m, 2H), 1.22 (d, J=6.2 Hz, 3H)

Formula XII was described as having fruity, green, fresh, woody, spicy and sweet notes.

Example VIII

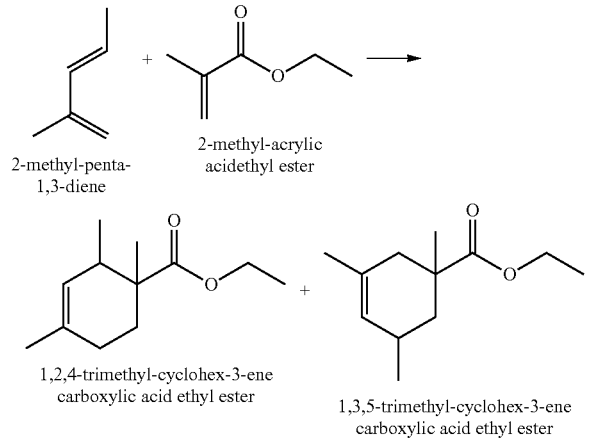

Preparation of 1,2,4-Trimethyl-cyclohex-3-enecarboxylic acid ethyl ester (Formula XIII) and 1,3,5-Trimethyl-cyclohex-3-enecarboxylic acid ethyl ester (Formula XIV)

2-Methyl-penta-1,3-diene (954 g) and 2-methyl-acrylic acidethyl ester (1.11 Kg) were charged into an autoclave and heated to 160° C. After 3 hours, the reaction temperature was increased to 220° C. (180 psi). The progress of the reaction was monitored with gas chromatography (GC) analysis. The reaction mixture was aged for about 8 hours and then distilled to afford a mixture of 1,2,4-trimethyl-cyclohex-3-enecarboxylic acid ethyl ester and 1,3,5-trimethyl-cyclohex-3-enecarboxylic acid ethyl ester (1.58 Kg). Formula XIII and Formula XIV had a weight ratio of about 95:5.

The mixture obtained in the above preparation possessed the NMR spectral characteristics of:

$^1$H NMR (400 MHz, CDCl$_3$): 5.10-5.29 (m, 1H), 4.09-4.17 (m, 2H), 2.11-2.75 (m, 1H), 1.86-1.97 (m, 2H), 1.55-1.68 (m, 2H), 1.64 (s, 3H), 1.26 (t, J=7.1 Hz, 3H), 1.19 (s, 3H), 0.88 (d, J=6.9 Hz, 3H)

The mixture of Formula XIII and Formula XIV was described as having fruity, fresh, earthy and herbaceous notes.

Example IX

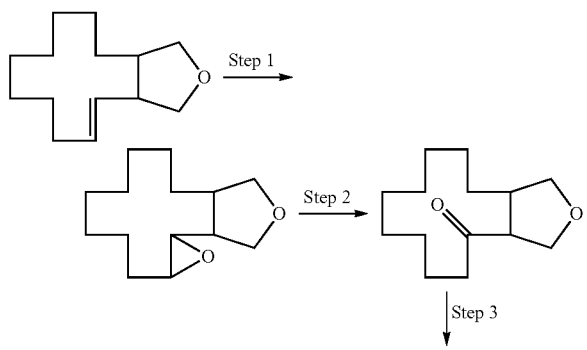

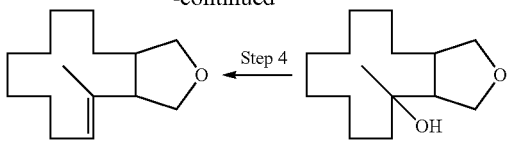

Preparation of 13-Methyl-3a,4,5,6,7,8,9,10,11,13a-decahydro-1H,3H-2-oxa-cyclopentacyclododecene (Formula XV)

13-Methyl-3a,4,5,6,7,8,9,10,11,13a-decahydro-1H,3H-2-oxa-cyclopentacyclododecene was prepared following below steps:

Step 1: Muscogene (478 g, 2.4 mol), sodium acetate (63 g, 0.76 mol) and ethyl acetate (500 mL) were charged into a flask. The reaction was cooled to 0° C. While the temperature was maintained at 0° C., peracetic acid (32%, 500 mL, 2.38 mol) was dropped in over an hour and the reaction mixture was stirred for another 2 hours. Saturated sodium carbonate solution (100 mL) and toluene (50 mL) were added. The organic layer was separated and washed with brine (200 mL). The crude was purified to provide 3,15-dioxa-tricyclo[11.3.0.0*2,4*]hexadecane (462 g, ~85% yield).

Step 2: 3,15-Dioxa-tricyclo[11.3.0.0*2,4*]hexadecane from Step 1 (260 g, 1.16 mol) was mixed with lithium iodide (2.5 g, 18.7 mmol) and heated to 200° C. for 8 hours. The reaction was then cooled down and washed with water (500 mL). The crude was distilled to provide dodecahydro-2-oxa-cyclopentacyclododecen-4-one (138 g, ~53% yield).

Step 3: Methyl magnesium chloride solution (3 M in THF, 190 mL, 0.56 mol) and toluene (100 mL) were mixed and heated to reflux. A solution of dodecahydro-2-oxa-cyclopentacyclododecen-4-one from Step 2 (0.56 mol) in toluene (100 mL) was then added in dropwise. The reaction mixture was stirred for another 2 hours and then cooled down. Acetic acid (200 g) and water (200 g) were added. The organic layer was separated and washed with brine (200 mL) to provide a crude containing 4-methyl-dodecahydro-2-oxa-cyclopentacyclododecen-4-ol.

Step 4: Crude 4-methyl-dodecahydro-2-oxa-cyclopentacyclododecen-4-ol (133 g) from Step 3 was dissolved in toluene (1 L). p-Toluenesulfonic acid (pTSA) (4 g) was added and the reaction was heated to reflux with a water trap. After 8 hours, there was no more water separated. The reaction was cooled and washed with sodium carbonate solution. Further distillation afforded 13-methyl-3a,4,5,6,7,8,9,10,11,13a-decahydro-1H,3H-2-oxa-cyclopentacyclododecene (101 g, ~82% yield).

$^1$H NMR (500 MHz, CDCl$_3$): 5.29 (m, 1H), 3.18-3.99 (m, 4H), 0.95-2.65 (m, 18H), 1.63 (s, 3H)

Formula XV was described as having fruity, woody, musky, clean, green, fresh, sweet and animalic notes with a unique tobacco-like quality.

What is claimed is:

1. A fragrance formulation containing an olfactory acceptable amount of a compound selected from the group consisting of:
    5-methyl-hept-5-enal;
    2,4-dimethyl-hex-4-enal; and
    a mixture thereof.
2. The fragrance formulation of claim 1, wherein the olfactory acceptable amount is from about 0.005 to about 50 weight percent of the fragrance formulation.

3. The fragrance formulation of claim 1, wherein the olfactory acceptable amount is from about 0.5 to about 25 weight percent of the fragrance formulation.

4. The fragrance formulation of claim 1, wherein the olfactory acceptable amount is from about 1 to about 10 weight percent of the fragrance formulation.

5. The fragrance formulation of claim 1 further comprising a product selected from the group consisting of a perfume, a cologne, toilet water, a cosmetic product, a personal care product, a fabric care product, a cleaning product, and an air freshener.

6. The fragrance formulation of claim 5, wherein the cleaning product is selected from the group consisting of a detergent, a dishwashing composition, a scrubbing compound, and a window cleaner.

7. The fragrance formulation of claim 1 further comprising a material selected from the group consisting of a polymer, an oligomer and a non-polymer.

8. The fragrance formulation of claim 7, wherein the non-polymer is selected from the group consisting of a surfactant, an emulsifier, a fat, a wax, a phospholipid, an organic oil, a mineral oil, a petrolatum, a natural oil, a perfume fixative, a fiber, a starch, a sugar and a solid surface material.

9. The fragrance formulation of claim 8, wherein the solid surface material is selected from the group consisting of zeolite and silica.

10. A method of improving, enhancing or modifying a fragrance formulation through the addition of an olfactory acceptable amount of a compound selected from the group consisting of:
   5-methyl-hept-5-enal;
   2,4-dimethyl-hex-4-enal; and
   a mixture thereof.

11. The method of claim 10, wherein the olfactory acceptable amount is from about 0.005 to about 50 weight percent of the fragrance formulation.

12. The method of claim 10, wherein the olfactory acceptable amount is from about 0.5 to about 25 weight percent of the fragrance formulation.

13. The method of claim 10, wherein the olfactory acceptable amount is from about 1 to about 10 weight percent of the fragrance formulation.

14. A fragrance product containing an olfactory acceptable amount of a compound selected from the group consisting of:
   5-methyl-hept-5-enal;
   2,4-dimethyl-hex-4-enal; and
   a mixture thereof.

15. The fragrance product of claim 14, wherein the fragrance product is selected from the group consisting of a perfume, a cologne, toilet water, a cosmetic product, a personal care product, a fabric care product, a cleaning product and an air freshener, a bar soap, a liquid soap, a shower gel, a foam bath, a cosmetic, a skin care product, a hair care product, a deodorant, an antiperspirant, a feminine care product, a baby care product, a family care product, a fabric product, an air care product, a fragrance delivery system, a cosmetic preparation, a cleaning agent, a disinfectant, a washing agent, a dental and oral hygiene product, a health care and nutritional product and a food product.

16. The fragrance product of claim 15, wherein the cleaning product is selected from the group consisting of a detergent, a dishwashing material, a scrubbing composition, a glass cleaner, a metal cleaner, a countertop cleaner, a floor cleaner, a carpet cleaner, a toilet cleaner and a bleach additive.

17. The fragrance product of claim 15, wherein the washing agent is selected from the group consisting of a laundry detergent and a rinse additive.

* * * * *